United States Patent
Tsai (10) Patent No.: US 9,782,586 B2
(45) Date of Patent: Oct. 10, 2017

(54) SIGNAL PROCESSING METHOD IN COCHLEAR IMPLANT

(71) Applicant: iMEDI PLUS Inc., Chupei, Hsinchu County (TW)

(72) Inventor: Kun Hsi Tsai, Chupei (TW)

(73) Assignee: iMEDI PLUS Inc., Hsinchu (TW)

( * ) Notice: Subject to any disclaimer, the term of this patent is extended or adjusted under 35 U.S.C. 154(b) by 0 days.

(21) Appl. No.: 14/838,298

(22) Filed: Aug. 27, 2015

(65) Prior Publication Data
US 2017/0056654 A1    Mar. 2, 2017

(51) Int. Cl.
*A61N 1/36* (2006.01)
*G10L 21/0224* (2013.01)
*G10L 19/00* (2013.01)

(52) U.S. Cl.
CPC .......... *A61N 1/36032* (2013.01); *G10L 19/00* (2013.01); *G10L 21/0224* (2013.01)

(58) Field of Classification Search
CPC .............. A61N 1/0541; A61N 1/36032; H04R 25/353; H04R 25/356; H04R 25/502; H04R 25/505
See application file for complete search history.

(56) References Cited

U.S. PATENT DOCUMENTS

| | | | |
|---|---|---|---|
| 7,027,987 B1* | 4/2006 | Franz | G10L 15/22 704/236 |
| 2004/0172242 A1* | 9/2004 | Seligman | H04R 25/356 704/225 |
| 2005/0111683 A1* | 5/2005 | Chabries | H03G 9/005 381/317 |
| 2009/0187065 A1* | 7/2009 | Basinger | A61N 1/36032 600/25 |

* cited by examiner

*Primary Examiner* — Eric D. Bertram
(74) *Attorney, Agent, or Firm* — Steven Reiss (57) ABSTRACT

A signal processing method in cochlear implant is performed by a speech processor and comprises a noise reduction stage and a signal compression stage. The noise reduction stage can efficiently reduce noise in a electrical speech signal of a normal speech. The signal compression stage can perform good signal compression to enhance signals to stimulate cochlear nerves of a hearing loss patient. The patient who uses a cochlear implant performing the signal processing method of the present invention can understand normal speech.

10 Claims, 7 Drawing Sheets

SIGNAL PROCESSING METHOD IN COCHLEAR IMPLANT

BACKGROUND OF THE INVENTION

1. Field of the Invention

The present invention relates to a signal processing method, and more particularly to a signal processing method in cochlear implant.

2. Description of Related Art

Cochlear implant is a surgically implanted electronic device that provides a sense of sound to hearing loss patients. The tremendous progress of the cochlear implant technologies has enabled many hearing loss patients to enjoy high level of speech understanding quality Noise reduction and signal compression are critical stages in the cochlear implant. For example, a conventional cochlear implant comprising multiple microphones can enhance the sensed speech volume. However, noises in the sensed speech are also amplified and compressed so as to affect the speech understanding of the hearing loss patient. Besides, the multiple microphones increase hardware cost.

SUMMARY OF THE INVENTION

An objective of the present invention is to provide a signal processing method in cochlear implant for computationally compressing an input speech signal into a predetermined amplitude range. The signal processing method is performed by a speech processor and comprises a noise reduction stage and a signal compression stage.

The noise reduction stage comprises:
receiving a t-th noisy frame $y_t$, wherein the t-th noisy frame $y_t$ is from an electrical speech signal y;
reducing noises in the t-th noisy frame $y_t$ to obtain a t-th clean frame $x_t$; and
outputting the t-th clean frame $x_t$.

The signal compression stage comprises:
receiving an amplitude envelope of the t-th clean frame $x_t$;
compressing the t-th clean frame $x_t$ to form a t-th output frame $z_t = \alpha_t \times (x_t - \bar{x}_t) + \bar{x}_t$, wherein
$\bar{x}_t$ is a mean of the amplitude envelope of the t-th clean frame $x_t$;
$\alpha_t$ is a compression factor;
when the t-th output frame $z_t$ is in a monitoring range between an upper boundary and a lower boundary, $\alpha_t = \alpha_{t-1} + \Delta\alpha_1$ and $\Delta\alpha_1$ is a positive value; and
when the t-th output frame $z_t$ is beyond the monitoring range, $\alpha_t = \alpha_{t-1} + \Delta\alpha_2$ and $\Delta\alpha_2$ is a negative value; and
outputting the t-th output frame $z_t$.

Another objective of the present invention is to provide a signal processing method in cochlear implant. The signal processing method is performed by a speech processor having a noise reduction unit and a signal compressor. The signal compressor has a compression unit, a boundary calculation unit, and a compression-factor-providing unit. The signal processing method comprises a noise reduction stage and a signal compression stage.

The noise reduction stage is performed by the noise reduction unit and comprises:
receiving a t-th noisy frame $y_t$, wherein the t-th noisy frame $y_t$ is from an electrical speech signal y;
reducing noises in the t-th noisy frame $y_t$ to obtain a t-th clean frame $x_t$; and
outputting the t-th clean frame $x_t$.

The signal compression stage is performed by the signal compressor and comprises:
receiving an amplitude envelope of the t-th clean frame $x_t$ by the compression unit and the boundary calculation unit;
calculating an upper boundary and a lower boundary and transmitting the upper boundary and the lower boundary to the compression-factor-providing unit by the boundary calculation unit;
compressing the t-th clean frame $x_t$ to obtain a t-th output frame $z_t$ and outputting the t-th output frame $z_t$ by the compression unit; and
calculating a compression factor $\alpha_t$ and transmitting the compression factor $\alpha_t$ to the compression unit by the compression-factor-providing unit according to the t-th output frame $z_t$, the upper boundary, and the lower boundary; wherein
$z_t = \alpha_t \times (x_t - \bar{x}_t) + \bar{x}_t$; and
$\bar{x}_t$ is a mean of an amplitude envelope of $x_t$, $t=1, \ldots T$, where T is the lengths of the current utterance;
when the t-th output frame $z_t$ is in a monitoring range between the upper boundary and the lower boundary, $\alpha_t = \alpha_{t-1} + \Delta\alpha_1$ and $\Delta\alpha_1$ is a positive value; and
when the t-th output frame $z_t$ is beyond the monitoring range, $\alpha_t = \alpha_{t-1} + \Delta\alpha_2$ and $\Delta\alpha_2$ is a negative value.

Based on the signal processing method of the present invention, the noise reduction stage can efficiently reduce noise in the electrical speech signal of the normal speech, and the signal compression stage can perform good signal compression to enhance signals to stimulate cochlear nerves of a hearing loss patient, such that the hearing loss patient can well understand the normal speech. The present invention performs the noise reduction stage and the signal compression stage to improve performance of the cochlear implant instead of using multiple microphones. Compared with the conventional cochlear implant with multiple microphones, the present invention would not increase the hardware cost.

Embodiments of the present invention are described in detail as follows.

DETAILED DESCRIPTION OF THE PREFERRED EMBODIMENT

Figure 1:
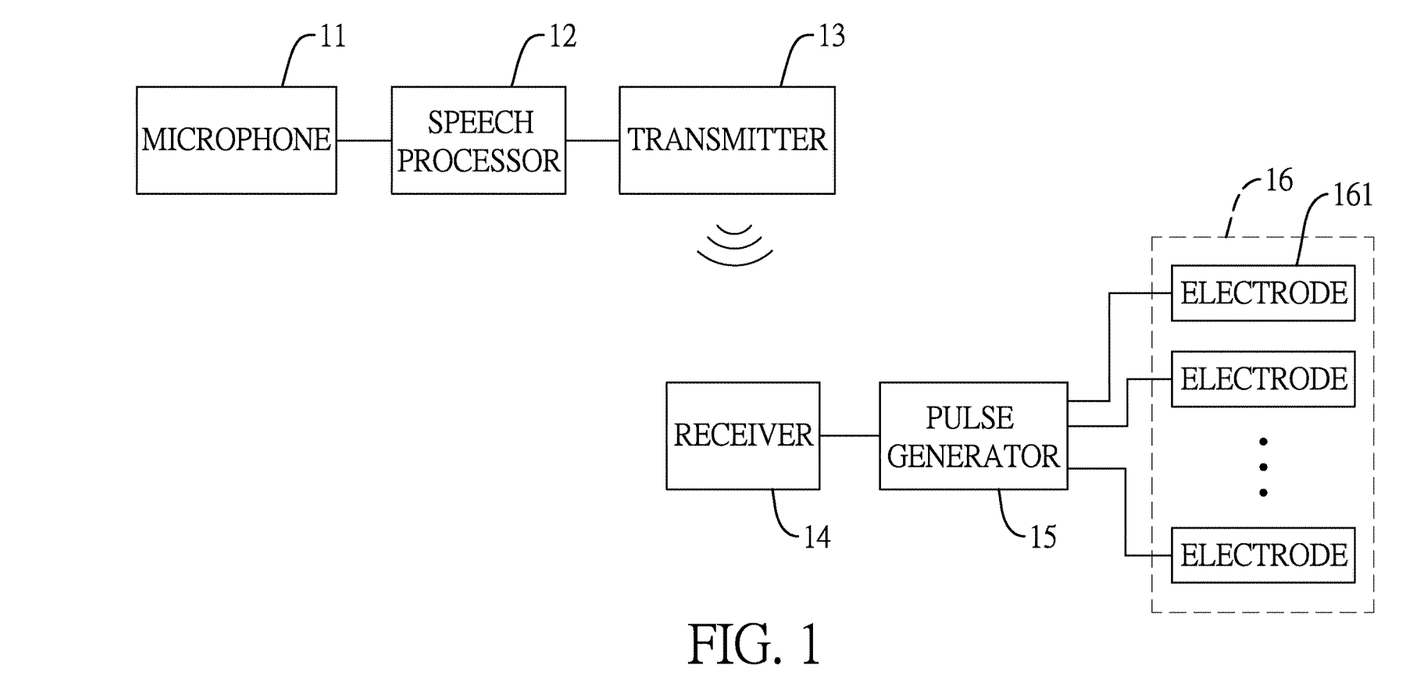
FIG. 1 is a circuit block diagram of a cochlear implant.

With reference to FIG. 1, a basic and conventional configuration of a circuit block diagram of a cochlear implant comprises a microphone 11, a speech processor 12, a transmitter 13, a receiver 14, a pulse generator 15, and an electrode array 16. The microphone 11 and the speech processor 12 are assembled to be mounted on a patient's ear. The transmitter 13 is adapted to be attached on an exterior surface of the patient's head skin. The receiver 14, the pulse generator 15, and the electrode array 16 are implanted under the patient's head skin.

The microphone 11 is an acoustic-to-electric transducer that converts a normal speech in air into an electrical speech signal. The speech processor 12 receives the electrical speech signal and converts the electrical speech signal into multiple output sub-speech signals in different frequencies. The transmitter 13 receives the output sub-speech signals from the speech processor 12 and wirelessly sends the output sub-speech signals to the receiver 14. The pulse generator 15 receives the output sub-speech signals from the receiver 14 and generates different electrical pulses based on the output sub-speech signals to the electrode array 16. The electrode array 16 has multiple electrodes 161 respectively and electrically connected to different cochlear nerves of the hearing loss patient's inner ear. Therefore, the electrodes 161 respectively output the electrical pulses to stimulate the cochlear nerves, such that the patient can hear something approximating the normal speech.

Figure 2:
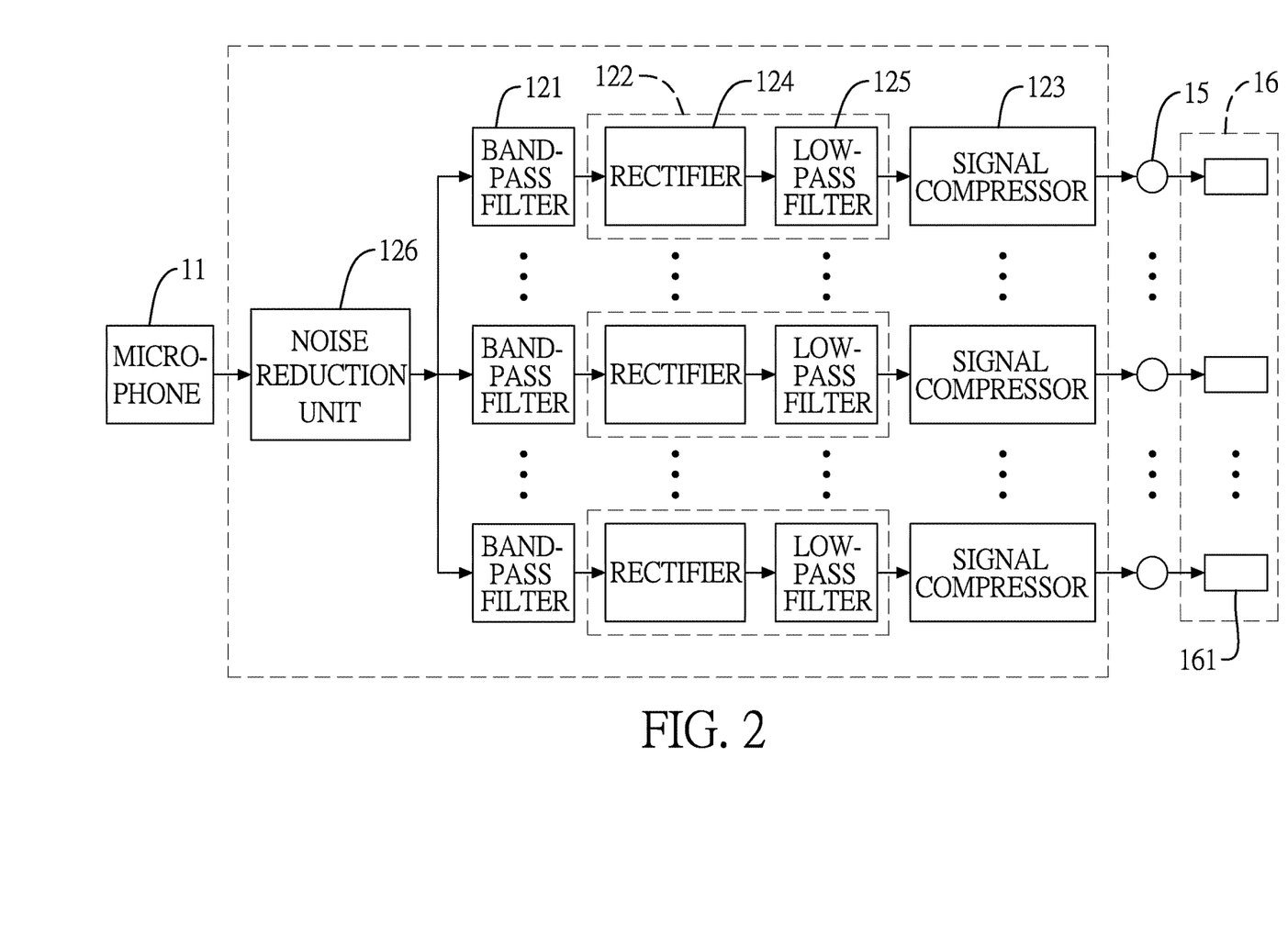
FIG. 2 is a detailed circuit diagram including a speech processor connected to a microphone and pulse generators of the present invention.

In more details, with reference to FIG. 2, the speech processor 12 has multiple channels including a first channel, a second channel, . . . , an i-th channel, . . . , and a n-th channel, wherein i and n are positive integrals. Each one of the channels has a band-pass filter 121, an envelope detection unit 122, and a signal compressor 123. The envelope detection unit 122 is used to detect an amplitude envelope of a signal and can have a rectifier 124 and a low-pass filter 125. In the present invention, a noise reduction unit 126 is added. The noise reduction unit 126 is connected between the microphone 11 and the band-pass filters 121 of each one of the channels. In time domain, when the noise reduction unit 126 receives the electrical speech signal from the microphone 11, the noise reduction unit 126 segments the electrical speech signal into several continuous frames to reduce noise of the frames. For example, when a time length of the electrical speech signal is 3 seconds, the noise reduction unit 126 can segment the electrical speech signal into 300 continuous frames, wherein a time length of each one of the frames of the electrical speech signal is 10 milliseconds.

Based on the above configuration, the band-pass filter 121 of each one of the channels sequentially receives the frames of the electrical speech signal from the noise reduction unit 126. The band-pass filter 121 of each one of the channels can preserve elements of each one of the frames of the electrical speech signal within a specific frequency band and remove elements beyond the specific frequency band from such frame. The specific frequency bands of the band-pass filters 121 of the channels are different from each other. Afterwards, the amplitude envelopes of the frames of the electrical speech signal are detected by the envelope detection units 122 and provided to the signal compressors 123 respectively.

The present invention relates to a noise reduction stage performed by the noise reduction unit 126 and a signal compression stage performed by the signal compressor 123. The noise reduction stage and the signal compression stage are respectively described below.

1. Noise Reduction Stage

The noise reduction unit 126 can be performed in a DDAE (deep denoising autoencoder)-based NR (noise reduction) structure. The DDAE-based NR structure is widely used in building a deep neural architecture for robust feature extraction and classification. In brief, with reference to FIG. 3, a single-layered DAE-based NR structure comprises an input layer 21, a hidden layer 22, and an output layer 23. The DDAE-based NR structure is a multiple-layered DAE-based NR structure comprising the input layer 21, the output layer 23, and multiple hidden layers 22. Because the parameter estimation and speech enhancement procedure of DDAE is the same as those of single-layered DAE, we only present the parameter estimation and speech enhancement for the single-layered DAE for ease of explanation. The same parameter estimation and speech enhancement procedures can be followed for the DDAE.

Figure 3:
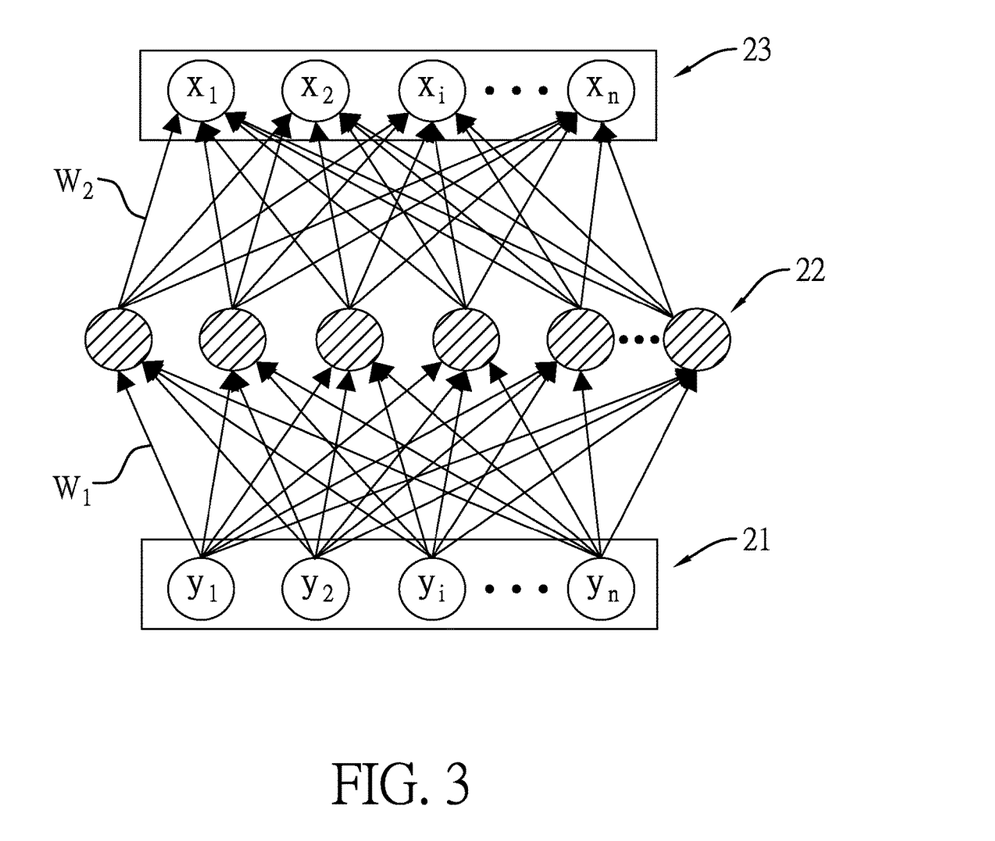
FIG. 3 is a schematic view of a single-layered DAE-based NR structure.

The input layer 21 receives an electrical speech signal y from the microphone 11 and segments the electrical speech signal y into a first noisy frame $y_1$, a second noisy frame $y_2$, . . . , a t-th noisy frame $y_t$, . . . , and a T-th noisy frame $y_T$, wherein T is a length of the current utterance. In other words, the present invention may segment an input speech signal, such as the electrical speech signal y, into a plurality of time-sequenced frames, such as the noisy frames $y_1$, $y_2$, . . . , and $y_T$. For the elements in the t-th noisy frame $y_t$, the noise reduction unit 126 reduces noise in the t-th noisy frame $y_t$ to form a t-th clean frame $x_t$. Afterwards, the output layer 23 sends the t-th clean frame $x_t$ to the channels of the speech processor 12 respectively.

A relationship between the t-th noisy frame $y_t$ and the t-th clean frame $x_t$ can be represented as:

$$x_t = W_2 h(y_t) + b_2 \quad (1)$$

where $h(y_t)$ is a function including $W_1$ and $b_1$ in time domain;

$W_1$ and $W_2$ are default connection weights in time domain; and $b_1$ and $b_2$ are default vectors of biases of the hidden layers 22 of the DDAE-based NR structure in time domain.

Besides, in another embodiment, the relationship between the t-th noisy frame $y_t$ and the t-th clean frame $x_t$ can be represented as $$x_t = \text{InvF}\{(W_2' h'(F\{y_t\}) + b_2')\} \quad (2)$$

where

F { } is a Fourier transform function to transfer the t-th noisy frame $y_t$ from time domain to frequency domain;

h'( ) is a function including $W_1'$ and $b_1'$;

$W_1'$ and $W_2'$ are default connection weights in frequency domain;

$b_1'$ and $b_2'$ are default vectors of biases of the hidden layers 22 of the DDAE-based NR structure in frequency domain; and InvF { } is an inverse Fourier transform function to obtain the t-th clean frame $x_t$.

According to experimental result, the t-th clean frame $x_t$ deduced from the Fourier transform and the inverse-Fourier transform as mentioned above has better performance than which without the Fourier transform and the inverse-Fourier transform.

For the time domain based method as shown in equation (1), $h(y_t)$ can be represented as:

$$h(y_t) = \sigma(W_1 y_t + b_1) = \frac{1}{1 + \exp[-(W_1 y_t + b_1)]} \quad (3)$$

For the frequency domain based method as shown in equation (2), h' (F $\{y_t\}$) can be represented as:

$$h'(F\{y_t\}) = \sigma(W_1'F\{y_t\} + b_1') = \frac{1}{1 + \exp[-(W_1'F\{y_t\} + b_1')]} \quad (4)$$

Regarding the parameters including $W_1$, $W_2$, $b_1$, and $b_2$ in time domain or $W_1'$, $W_2'$, $b_1'$, and $b_2'$ in frequency domain, they are preset in the speech processor 12.

For example, in time domain, the parameters including $W_1$, $W_2$, $b_1$, and $b_2$ in equations (1) and (3) are obtained from a training stage. Training data including a clean speech sample u and a corresponding noisy speech sample v. Likewise, the clean speech sample u is segmented into several clean frames $u_1, u_2, \ldots, u_{T'}$, and the noisy speech sample v is segmented into several noisy frames $v_1, v_2, \ldots, v_{T'}$, wherein T' is a lengths of a training utterance.

The parameters including $W_1$, $W_2$, $b_1$, and $b_2$ of equation (1) and equation (3) are optimized based on the following objective function:

$$\theta^* = \arg\min_\theta \left( \frac{1}{T'} \sum_{t=1}^{T'} \|u_t - \bar{u}_t\|_2^2 + \eta(\|W_1\|_2^2 + \|W_2\|_2^2) \right) \quad (5)$$

In equation (5), θ is a parameter set $\{W_1, W_2, b_1, b_2\}$, T' is a total number of the clean frames $u_1, u_2, \ldots, u_{T'}$, and η is a constant used to control the tradeoff between reconstruction accuracy and regularization on connection weights (for example, η can be set as 0.0002). The training data including the clean frames $u_1, u_2, \ldots, u_{T'}$ and the training parameters of $W_{1\text{-}test}$, $W_{2\text{-}test}$, $b_{1\text{-}test}$ and $b_{2\text{-}test}$ can be substituted into the equation (1) and equation (3) to obtain a reference frame $\bar{u}_t$. When the training parameters of $W_{1\text{-}test}$, $W_{2\text{-}test}$, $b_{1\text{-}test}$, and $b_{2\text{-}test}$ can make the reference frame $\bar{u}_t$, mostly approximate the clean frames $u_t$, such training parameters of $W_{1\text{-}test}$, $W_{2\text{-}test}$, $b_{1\text{-}test}$, and $b_{2\text{-}test}$ are taken as the parameters of $W_1$, $W_2$, $b_1$, and $b_2$ of equation (1) and equation (3). Besides, when the noisy speech sample v approximates the electrical speech signal y, the training result of the parameters of $W_1$, $W_2$, $b_1$, and $b_2$ can be optimized. The optimization of equation (5) can be solved by using any unconstrained optimization algorithm. For example, a Hessian-free algorithm can be applied in the present invention.

After training, optimized parameters including $W_1$, $W_2$, $b_1$, and $b_2$ are obtained to be applied to equation (1) and equation (3) for real noise reduction application.

Besides, in frequency domain, the parameters including $W_1'$, $W_2'$, $b_1'$, and $b_2'$ of equation (2) and equation (4) are optimized based on the following objective function:

$$\theta^* = \arg\min_\theta \left( \frac{1}{T'} \sum_{t=1}^{T'} \|u_t - \bar{u}_t\|_2^2 + \eta(\|W_1'\|_2^2 + \|W_2'\|_2^2) \right) \quad (6)$$

In equation (6), θ is a parameter set $\{W_1', W_2', b_1', b_2'\}$, T' is a total number of the clean frames $u_1, u_2, \ldots, u_{T'}$, and η is a constant used to control the tradeoff between reconstruction accuracy and regularization on connection weights (for example, η can be set as 0.0002). The training data including the clean frames $u_1, u_2, \ldots, u_{T'}$ and the training parameters of $W_{1\text{-}test}'$, $W_{2\text{-}test}'$, $b_{1\text{-}test}'$, and $b_{2\text{-}test}'$ can be substituted into the equation (2) and equation (4) to obtain a reference frame $\bar{u}_t$. When the training parameters of $W_{1\text{-}test}'$, $W_{2\text{-}test}'$, $b_{1\text{-}test}'$, and $b_{2\text{-}test}'$ can make the reference frame $\bar{u}_t$, mostly approximate the clean frames $u_t$, such training parameters of $W_{1\text{-}test}'$, $W_{2\text{-}test}'$, $b_{1\text{-}test}'$, and $b_{2\text{-}test}'$ are taken as the parameters of $W_1'$, $W_2'$, $b_1'$, and $b_2'$ of equation (2) and equation (4). Besides, when the noisy speech sample v approximates the electrical speech signal y, the training result of the parameters of $W_1'$, $W_2'$, $b_1'$, and $b_2'$ can be optimized. The optimization of equation (6) can be solved by using any unconstrained optimization algorithm. For example, a Hessian-free algorithm can be applied in the present invention.

After training, optimized parameters including $W_1'$, $W_2'$, $b_1'$, and $b_2'$ are obtained to be applied to equation (2) and equation (4) for real noise reduction application.

Figure 4A:
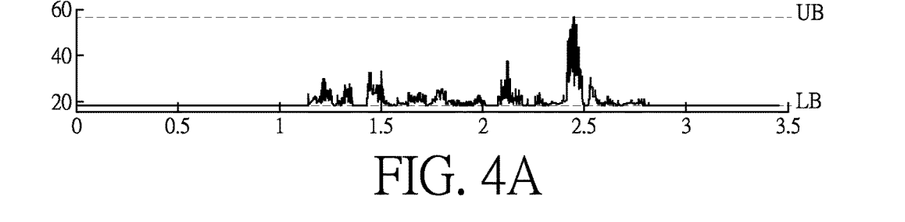
FIG. 4A shows an amplitude envelope of a clean speech signal.
Figure 4B:
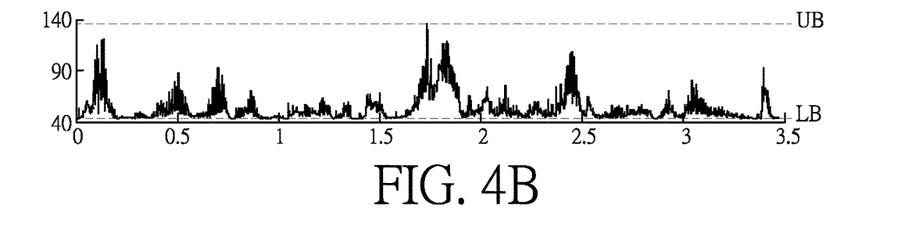
FIG. 4B shows an amplitude envelope of a noisy speech signal.
Figure 4C:
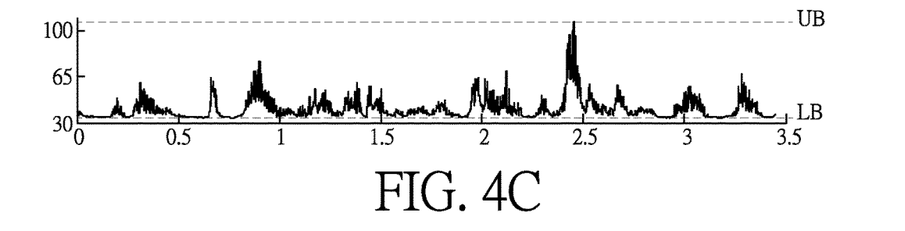
FIG. 4C shows an amplitude envelope detected by a conventional log-MMSE estimator.
Figure 4D:
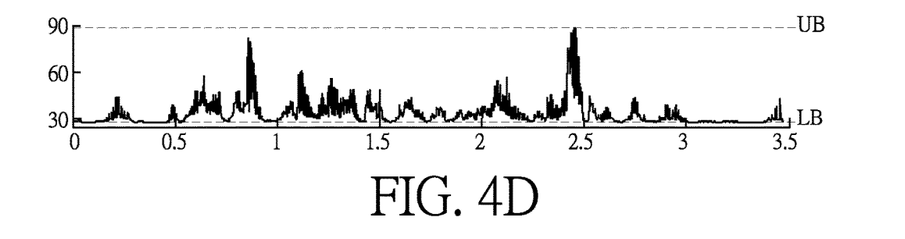
FIG. 4D shows an amplitude envelope detected by a conventional KLT estimator.
Figure 4E:
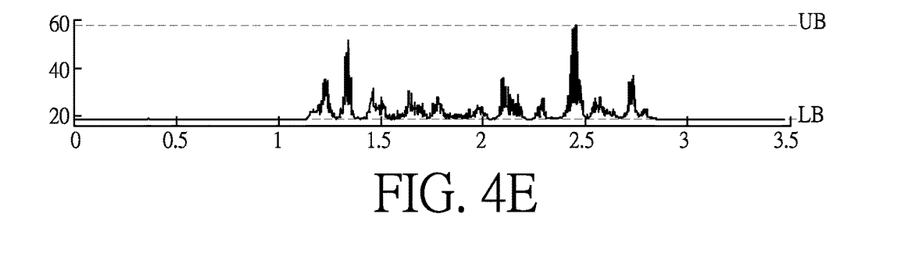
FIG. 4E shows an amplitude envelope detected by the present invention.

With reference to FIGS. 4A and 4B, FIG. 4A shows an amplitude envelope of a clean speech signal and FIG. 4B shows an amplitude envelope of a noisy speech signal. FIG. 4C shows an amplitude envelope detected by a conventional log-MMSE (minimum mean square error) estimator. FIG. 4D shows an amplitude envelope detected by a conventional KLT (Karhunen-Loeve transform) estimator. FIG. 4E shows an amplitude envelope detected by the present invention. Comparing FIG. 4E with FIG. 4A, the detection result of the present invention is most approximate to the clean speech signal, which means the noise is removed. Comparing FIG. 4B with FIGS. 4C and 4D, the detection results as illustrated in FIGS. 4C and 4D are still noisy. According to experimental result as mentioned above, the signal performances of the conventional log-MMSE estimator and the KLT estimator are not as good as the present invention. The present invention has better noise reducing efficiency.

2. Signal Compression Stage

Figure 5:
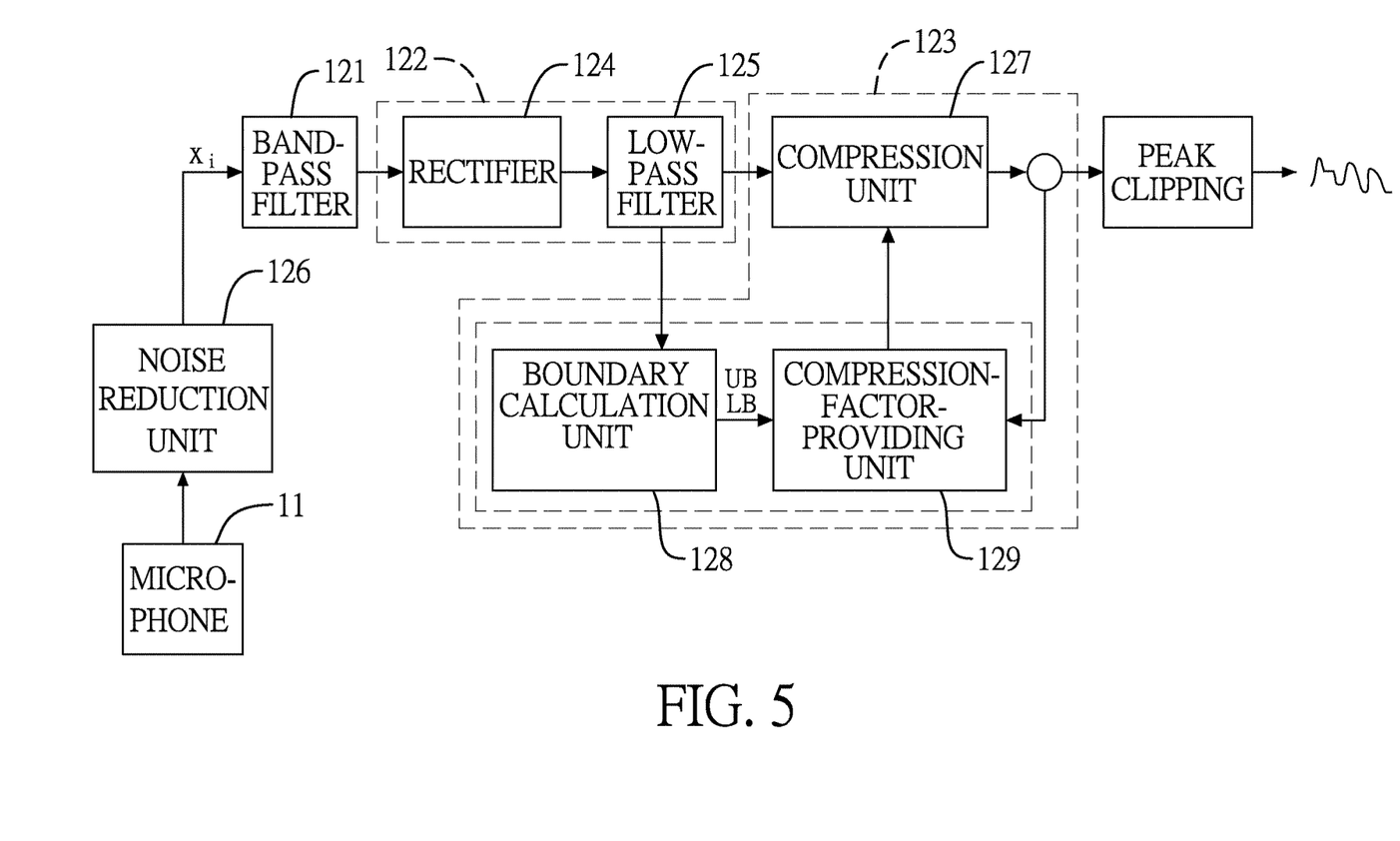
FIG. 5 is a circuit block diagram of one channel of the speech processor of the present invention.
Figure 6:
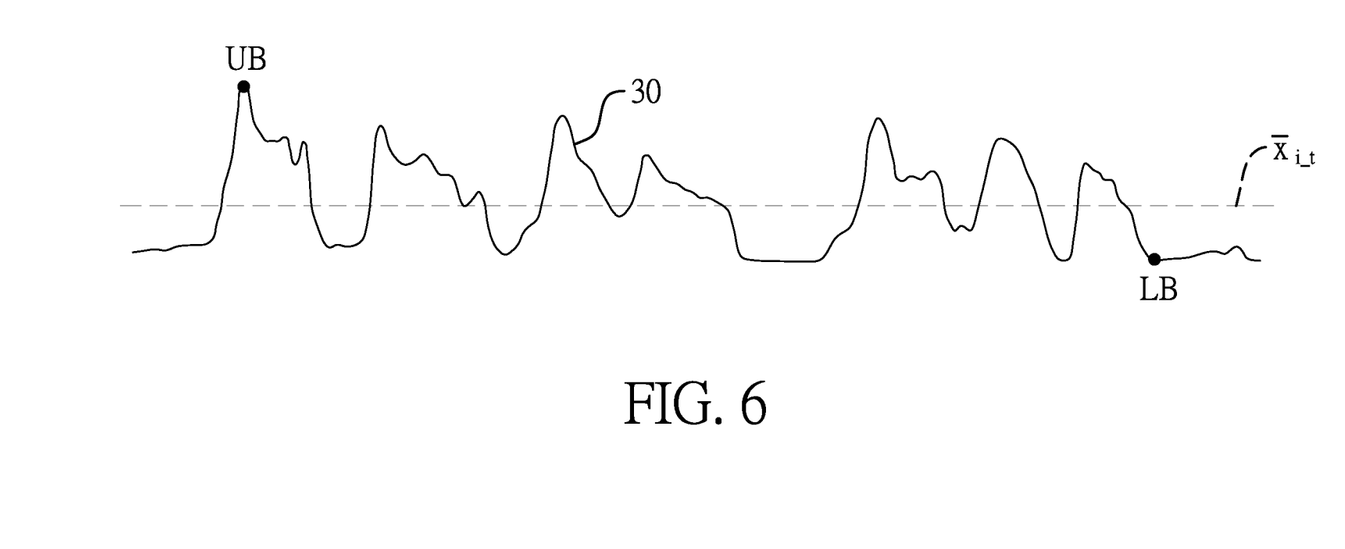
FIG. 6 is a waveform diagram of an amplitude envelope detected by an envelope detection unit.

With reference to FIGS. 2 and 5, for the i-th channel of the speech processor 12, the signal compressor 123 receives an amplitude envelope of the t-th clean frame $x_t$ within the specific frequency band from the noise reduction unit 126 through the band-pass filter 121 and the envelope detection unit 122. The amplitude envelope 30 of the t-th clean frame $x_t$ is illustrated in FIG. 6. As shown in FIG. 6, the amplitude envelope 30 of t-th clean frame $x_t$ is time-varying.

The signal compressor 123 of the present invention comprises a compression unit 127, a boundary calculation unit 128, and a compression-factor-providing unit 129. The compression unit 127 and the boundary calculation unit 128 are connected to the envelope detection unit 122 to receive the amplitude envelope 30 of the t-th clean frame $x_t$, real-time. With reference to FIGS. 5 and 6, the boundary calculation unit 128 can detect an upper boundary UB and a lower boundary LB in the amplitude envelope of the t-th clean frame $x_t$. The calculation result of the upper boundary UB and the lower boundary LB are transmitted to the compression-factor-providing unit 129. The upper boundary UB and the lower boundary LB can be calculated by:

$$UB = \bar{x}_t + \alpha_0 \times (\max(x_t) - \bar{x}_t) \quad (7)$$

$$LB = \bar{x}_t + \alpha_0 \times (\min(x_t) - \bar{x}_t) \quad (8)$$

where $\alpha_0$ is an initial value.

The compression unit 127 receives the amplitude envelope 30 of the t-th clean frame $x_t$, and outputs a t-th output frame $z_t$. Inputs of the compression-factor-providing unit 129 is connected to an input of the compression unit 127, an output of the compression unit 127, and an output of the boundary calculation unit 128 to receive a calculating result of the upper boundary UB, the lower boundary LB, and the t-th output frame $z_t$. An output of the compression-factorproviding unit 129 is connected to the input of the compression unit 127, such that the compression-factor-providing unit 129 provides a compression factor $\alpha_t$ to the compression unit 127. The compression factor $\alpha_t$ is determined according to a previous compression factor $\alpha_{t-1}$, the upper boundary UB, the lower boundary LB, and the t-th output frame $z_t$. In brief, the present invention may determine the compression factor $\alpha_t$ for a frame based on the frame's amplitude upper boundary UB and lower boundary LB. When the t-th output frame $z_t$ is in a monitoring range between the upper boundary UB and the lower boundary LB, the compression factor $\alpha_t$ is expressed as:

$$\alpha_t = \alpha_{t-1} + \Delta\alpha_1 \quad (9)$$

where $\Delta\alpha_1$ is a positive value (i.e., $\Delta\alpha_1 = 1$).

In contrast, when the t-th output frame $z_t$ is beyond the monitoring range, the compression factor $\alpha_t$ is expressed as:

$$\alpha_t = \alpha_{t-1} + \Delta\alpha_2 \quad (10)$$

where $\Delta\alpha_2$ is a negative value (i.e., $\Delta\alpha_2 = -0.1$).

The t-th output frame $z_t$ can be expressed as:

$$z_t = \alpha_t \times (x_t - \bar{x}_t) + \bar{x}_t \quad (11)$$

where $\bar{x}_t$ is a mean of the amplitude envelope of the t-th clean frame $x_t$.

Figure 7:
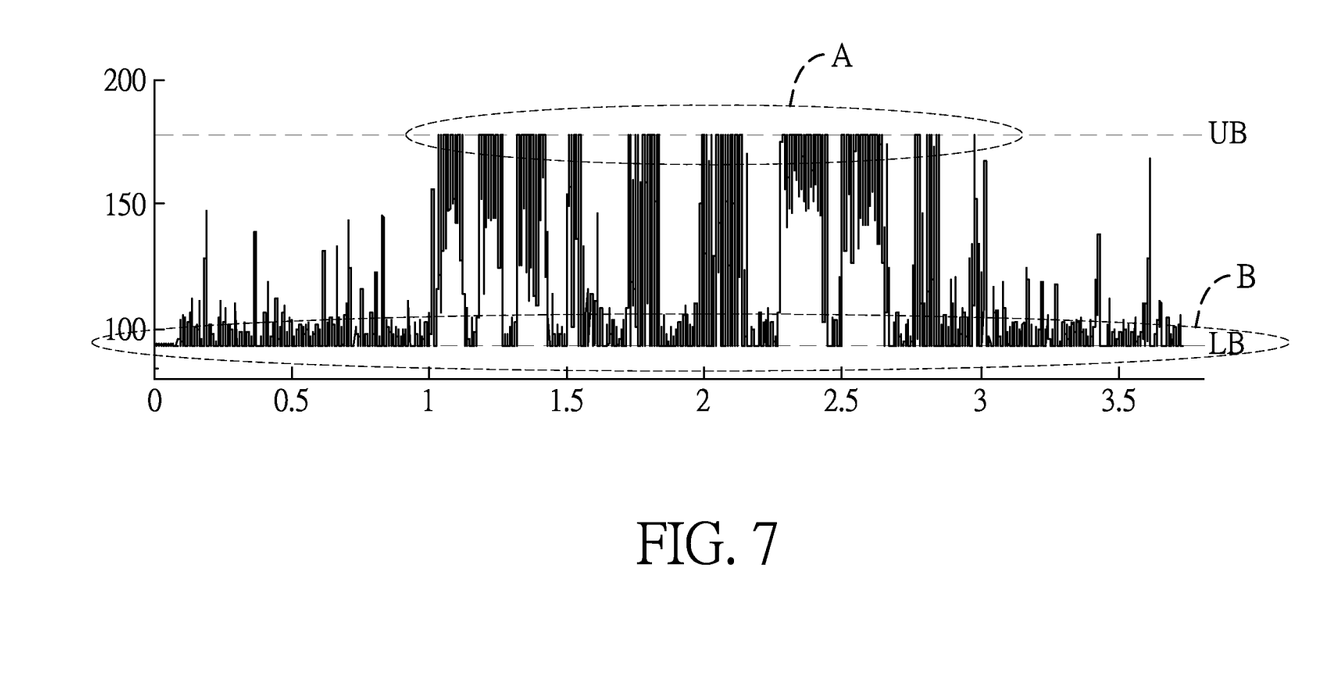
FIG. 7 is a waveform diagram of an output frame generated by the signal compressor of the present invention.

According to equations (9) and (10), a present compression factor $\alpha_t$ is obtained by a previous compression factor $\alpha_{t-1}$. It is to be understood that the present invention may modify the compression factor $\alpha_t$, for the next frame based on the next frame's amplitude upper boundary UB and lower boundary LB. According to equation (11), the t-th output frame $z_t$, is repeatedly adjusted by the t-th clean frame $x_t$, and the calculation result of UB, LB, and $\alpha_t$. According to experimental result, the signal compression capability is good. As illustrated in FIG. 7, speech components A in the t-th output frame $z_t$, are amplified. The speech components A even reach the upper boundary UB. In contrast, noise components B are not exactly amplified. Therefore, the t-th output frame $z_t$ is enhanced to stimulate the cochlear nerves. The user can accurately understand a conversation.

What is claimed is:

1. A signal processing method for a cochlear implant, wherein the cochlear implant comprises a microphone and a speech processor, the microphone is configures to convert sound into an electrical speech signal y, the speech processor is configured to receive the electrical speech signal y, process the electrical speech signal y, and output the processed electrical speech signals; the signal processing method comprising:
   a noise reduction stage performed by the speech processor, comprising:
      receiving the electrical speech signal y from the microphone;
      segmenting the electrical speech signal y to a plurality of continuous noisy frames, the plurality of continuous noisy frames comprising a first noisy frame $y_1$, a second noisy frame $y_2$, ..., a t-th noisy frame $y_t$, ..., and T-th noisy frame $y_T$ wherein T is a length of the sound;
      reducing noises in the t-th noisy frame $y_t$ to obtain a t-th clean frame $x_t$; and
      outputting the t-th clean frame $x_t$; and
   a signal compression stage performed by the speech processor, comprising:
      receiving an amplitude envelope of the t-th clean frame $x_t$;
      compressing the amplitude envelope of the t-th clean frame $x_t$ to form a t-th output frame $z_t = \alpha_t \times (x_t - \bar{x}_t) + \bar{x}_t$, wherein
         $\bar{x}_t$ is a mean of the amplitude envelope of the t-th clean frame $x_t$;
         $\alpha_t$ is a compression factor;
         when the t-th output frame $z_t$ is in a monitoring range between an upper boundary and a lower boundary, $\alpha_t = \alpha_{t-1} + \Delta\alpha_1$ and $\Delta\alpha_1$ is a positive value; and
         when the t-th output frame $z_t$ is beyond the monitoring range, $\alpha_t = \alpha_{t-1} + \Delta\alpha_2$ and $\Delta\alpha_2$ is a negative value; and
      outputting the t-th output frame $z_t$.

2. The signal processing method as claimed in claim 1, wherein the t-th clean frame $x_t$ in the noise reduction stage is expressed as $$x_t = W_2 h(y_t) + b_2$$

where
   $h(y_t)$ is a function including $W_1$ and $b_1$ in time domain;
   $W_1$ and $W_2$ are default connection weights in the time domain; and
   $b_1$ and $b_2$ are default vectors of biases of hidden layers of a DDAE (deep denoising autoencoder)-based NR (noise reduction) structure in the time domain.

3. The signal processing method as claimed in claim 2, wherein $h(y_t)$ in the noise reduction stage is expressed as $$h(y_t) = \frac{1}{1 + \exp[-(W_1 y_t + b_1)]}.$$

4. The signal processing method as claimed in claim 3, wherein the upper boundary in the signal compression stage is expressed as:

$$UB = \bar{x}_t + \alpha_0 \times (\max(x_t) - \bar{x}_t); \text{ and}$$

the lower boundary in the signal compression stage is expressed as:

$$LB = \bar{x}_t + \alpha_0 \times (\min(x_t) - \bar{x}_t).$$

5. The signal processing method as claimed in claim 2, wherein the upper boundary in the signal compression stage is expressed as:

$$UB = \bar{x}_t + \alpha_0 \times (\max(x_t) - \bar{x}_t); \text{ and}$$

the lower boundary in the signal compression stage is expressed as:

$$LB = \bar{x}_t + \alpha_0 \times (\min(x_t) - \bar{x}_t).$$

6. The signal processing method as claimed in claim 1, wherein the t-th clean frame $x_t$, in the noise reduction stage is expressed as $$x_t = InvF\{(W_2' h'(F\{y_t\}) + b_2')\}$$

where $F\{\}$ is a Fourier transform function to transfer the t-th noisy frame $y_t$ from time domain to frequency domain;
   $h'()$ is a function including $W_1'$ and $b_1'$;
   $W_1'$ and $W_2'$ are default connection weights in frequency domain;
   $b_1'$ and $b_2'$ are default vectors of biases of hidden layers of a DDAE-based NR structure in frequency domain; and
   $InvF\{\}$ is an inverse Fourier transform function to obtain the t-th clean frame $x_t$.

7. The signal processing method as claimed in claim 6, wherein h' (F {yt}) in the noise reduction stage is expressed as $$h'(F\{y_t\}) = \frac{1}{1 + \exp[-(W'_1 F\{y_t\} + b'_1)]}.$$

8. The signal processing method as claimed in claim 7, wherein the upper boundary in the signal compression stage is expressed as:

UB=$\bar{x}_t$+$\alpha_0$×(max($x_t$)−$\bar{x}_t$); and the lower boundary in the signal compression stage is expressed as:

LB=$\bar{x}_t$+$\alpha_0$×(min($x_t$)−$\bar{x}_t$).

9. The signal processing method as claimed in claim 6, wherein the upper boundary in the signal compression stage is expressed as:

UB=$\bar{x}_t$+$\alpha_0$×(max($x_t$)−$\bar{x}_t$); and the lower boundary in the signal compression stage is expressed as:

LB=$\bar{x}_t$+$\alpha_0$×(min($x_t$)−$\bar{x}_t$).

10. The signal processing method as claimed in claim 1, wherein the upper boundary in the signal compression stage is expressed as:

UB=$\bar{x}_t$+$\alpha_0$×(max($x_t$)−$\bar{x}_t$); and the lower boundary in the signal compression stage is expressed as:

LB=$\bar{x}_t$+$\alpha_0$×(min($x_t$)−$\bar{x}_t$).

* * * * *